United States Patent [19]

Martinez

[11] Patent Number: 4,986,622

[45] Date of Patent: Jan. 22, 1991

[54] FIBER OPTIC LIGHT TRANSMISSION APPARATUS

[76] Inventor: Miguel Martinez, 1880 W. Sunset Knoll La., Tucson, Ariz. 85704

[21] Appl. No.: 363,214

[22] Filed: Jun. 8, 1989

[51] Int. Cl.⁵ .......................... G02B 6/26; F21V 7/04; A61B 1/06

[52] U.S. Cl. ............... 350/96.15; 350/96.21; 350/96.22; 350/96.26; 350/96.20; 362/32; 362/263; 362/264; 128/4; 128/6

[58] Field of Search ............... 350/96.10, 96.15, 96.18, 350/96.20, 96.21, 96.22, 96.24, 96.25, 96.26, 96.23; 362/32, 157, 263, 264; 606/11, 15, 16; 128/4, 6

[56] References Cited

U.S. PATENT DOCUMENTS

| | | | |
|---|---|---|---|
| 3,382,353 | 5/1968 | Wappler | 362/32 X |
| 4,669,819 | 6/1987 | Hengst et al. | 350/96.20 |
| 4,756,597 | 7/1988 | Hahn et al. | 350/96.26 |
| 4,776,668 | 10/1988 | Fujimoto | 350/96.26 |
| 4,850,669 | 7/1989 | Welker et al. | 350/96.20 |
| 4,870,952 | 10/1989 | Martinez | 128/23 |
| 4,900,122 | 2/1990 | Frank et al. | 350/96.20 |
| 4,919,508 | 4/1990 | Grace et al. | 350/96.20 |

FOREIGN PATENT DOCUMENTS

60-218615  11/1985  Japan .......................... 350/96.26 X

Primary Examiner—Brian Healy

[57] ABSTRACT

It is a problem in the field of light transmission systems to use unbreakable heat sensitive light guides such as plastic optical fibers, with a high thermal output light source. The heat sensitive light guide is damaged by the thermal output of the light source when placed in close proximity thereto. The improved light transmission apparatus uses heat sensitive plastic optical fibers as the primary light guide and uses a heat resistant interface to couple the plastic optical fibers to the light source. In the preferred embodiment, this interface is an optically conductive media that has high thermal attenuation and is interposed between the high thermal output light source and the heat sensitive plastic optical fibers. This interface can be a short length of glass optical fiber light guide as is used in the prior art.

31 Claims, 3 Drawing Sheets

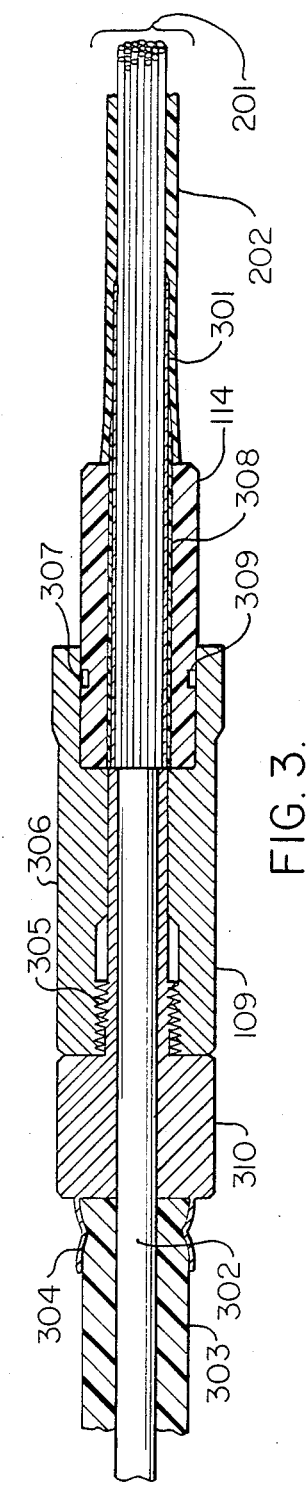
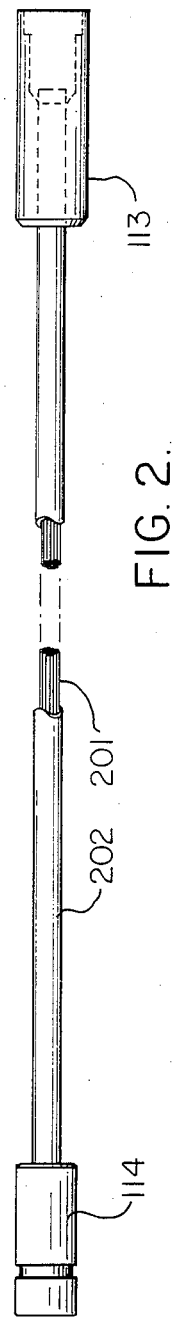
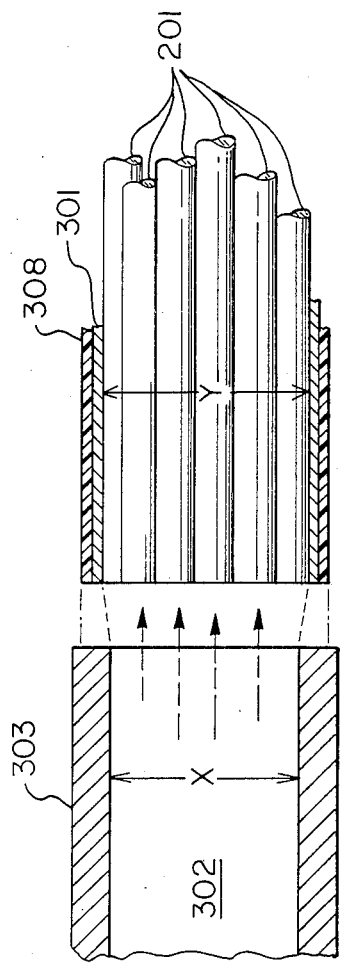
FIG. 3.
FIG. 2.
FIG. 6.

FIBER OPTIC LIGHT TRANSMISSION APPARATUS

FIELD OF THE INVENTION

This invention relates to light transmission systems and, in particular, to an improved fiber optic light transmission apparatus for use in medical or industrial systems.

PROBLEM

It is a problem in the field of light transmission systems to use heat sensitive light guides, such as plastic optical fibers, with a high thermal output light source. The heat sensitive light guide is damaged by the thermal output of the light source when placed in close proximity thereto. This phenomenon has prevented the use of heat sensitive light guides, such as plastic optical fibers, in many applications where a high intensity light source is required.

The conventional approach to solving this problem is to use heat resistant light guides, such as glass optical fibers, in this environment. The glass optical fibers can be placed near the light source without suffering damage. The light source produces a light beam that is focused on a predetermined size aperture a fixed distance from the light source. It is important to locate the input of the light guide at the light source focal point to minimize the light loss. The problem with glass optical fibers is that they are significantly more expensive than plastic optical fibers and more brittle. Such a glass light guide has a limited lifetime due to its brittle nature and the hostile environment in which it is used. Other types of heat resistant light guides used in this application are manufactured from quartz glass fibers or liquid filled cables such as the Thackray 57-4570 light transmission cable.

An example of a typical high light intensity application is the use of glass optical fibers in the field of medical systems. In this application, a light source comprising a mercury vapor or metal halide gas discharge lamp generates a high intensity beam of light. The beam of light is carried by a glass optical fiber light guide to an instrument such as an arthroscope which is inserted into a patient's knee joint. An intense light is required in this application in order to properly illuminate the inside of the knee joint during the surgical procedure. The illumination must be of great enough intensity to enable the arthroscope camera to project a clear image of the joint on a video display. In addition, the glass optical fiber light guide must be covered with a medical grade jacket since it is used in a surgical environment. The resultant expense of this light guide requires that the light guide be reusable. The light guide is typically sterilized after each surgical procedure either by autoclaving or cold solution sterilization in a disinfectant such as alcohol, glutaraldehyde or ethylene oxide (ETO). This requires the use of a chemically resistant jacket on the glass optical fiber light guide. A heat resistant connector such as stainless steel is also required at one end of the light guide to connect to the light source and at the other end of the light guide to connect to the arthroscope. The resultant light guide is expensive, heavy and somewhat difficult to bend. The existing light guides of this sort typically have a length on the order of six to nine feet. This requires that the light source be placed in close proximity to the patient during surgery. In addition, an arthroscopic procedure typically takes three hours or more and the surgeon must contend with a bulky and heavy light guide in performing this delicate procedure using the arthroscope.

SOLUTION

The above described problems are solved and a technical advance achieved in the field by the improved fiber optic light transmission apparatus of the present invention. This improved light transmission apparatus uses unbreakable heat sensitive plastic optical fibers as the primary light guide and uses a heat resistant interface to couple the plastic optical fibers to the high intensity, high thermal output light source. In the preferred embodiment, this interface is an optically conductive media that has high thermal attenuation and is interposed between the high thermal output light source and the heat sensitive plastic optical fibers.

This interface can be a short length of glass optical fiber light guide as is used in the prior art. The glass optical fiber light guide can withstand the high thermal output of the light source at one end and produces the required high intensity light beam at the other end thereof without the corresponding high thermal output. The plastic optical fiber light guide is coupled to the end of the glass optical fiber light conductor by the use of a simple connector.

To avoid optical mismatch and the heat generated as the result of such a mismatch, the optical cross section of the heat sensitive light conductor is equal to or greater than the optical cross section of the heat resistant light conductor. The optical cross section limitation is critical since the light intensity of the light source is such that an optical mismatch at the coupling between the heat sensitive light conductor and the heat resistant light conductor instantaneously causes the generation of a significant amount of heat. This heat is sufficient to damage the heat sensitive light conductor so that it no longer is able to conduct light. In the case of less intense light, this optical mismatch is not a significant problem.

The plastic optical fiber light guide provides a significant advantage in a medical environment since it is inexpensive and is therefore disposable. An additional cost savings is realized by the fact that the plastic optical fiber light guide can be presterilized and pre-packaged. The specific implementation illustrated herein uses a plurality of individual small diameter plastic optical fibers which enables the cable to be curved in a very tight radius blend. These plastic optical fibers also have the optical conductivity required to transmit a high intensity light beam.

BRIEF DESCRIPTION OF THE DRAWING

FIG. 2 illustrates a typical plastic optical fiber light guide;

FIG. 3 illustrates the interconnection of the heat resistant light conductor with the heat sensitive light conductor;

FIG. 6 illustrates the relative optical crosssections of the heat resistant light conductor and the heat sensitive light conductor.

DETAILED DESCRIPTION

It is a problem in the field of light transmission systems to use unbreakable heat sensitive light guides such as plastic optical fibers, with a high thermal output light source. The heat sensitive light guide is damaged by the high thermal output of the light source when placed in close proximity thereto. This phenomenon has prevented the use of heat sensitive light guides, such as plastic optical fibers, in many applications where a high intensity light source is required.

The improved light transmission apparatus of this invention uses heat sensitive plastic optical fibers as the primary light guide and uses a heat resistant interface to couple the plastic optical fibers to the light source. In the preferred embodiment, this interface is an optically conductive media that has high thermal attenuation and is interposed between the high thermal output light source and the heat sensitive plastic optical fibers.

This interface can be a short length of glass optical fiber light guide as is used in the prior art. The glass optical fiber light guide can withstand the high thermal output of the light source at one end and produces the required high intensity light beam at the other end thereof without the corresponding high thermal output. The plastic optical fiber light guide is coupled to the end of the glass optical fiber light conductor by the use of a simple connector.

To avoid optical mismatch and the heat generated as the result of such a mismatch, the optical cross section of the heat sensitive light conductor is equal to or greater than the optical cross section of the heat resistant light conductor. The optical cross section limitation is critical since the light intensity of the light source is such that an optical mismatch at the coupling between the heat sensitive light conductor and the heat resistant light conductor instantaneously causes the generation of a significant amount of heat. This heat is sufficient to damage the heat sensitive light conductor so that it no longer is able to conduct light.

System Architecture

Figure 1:
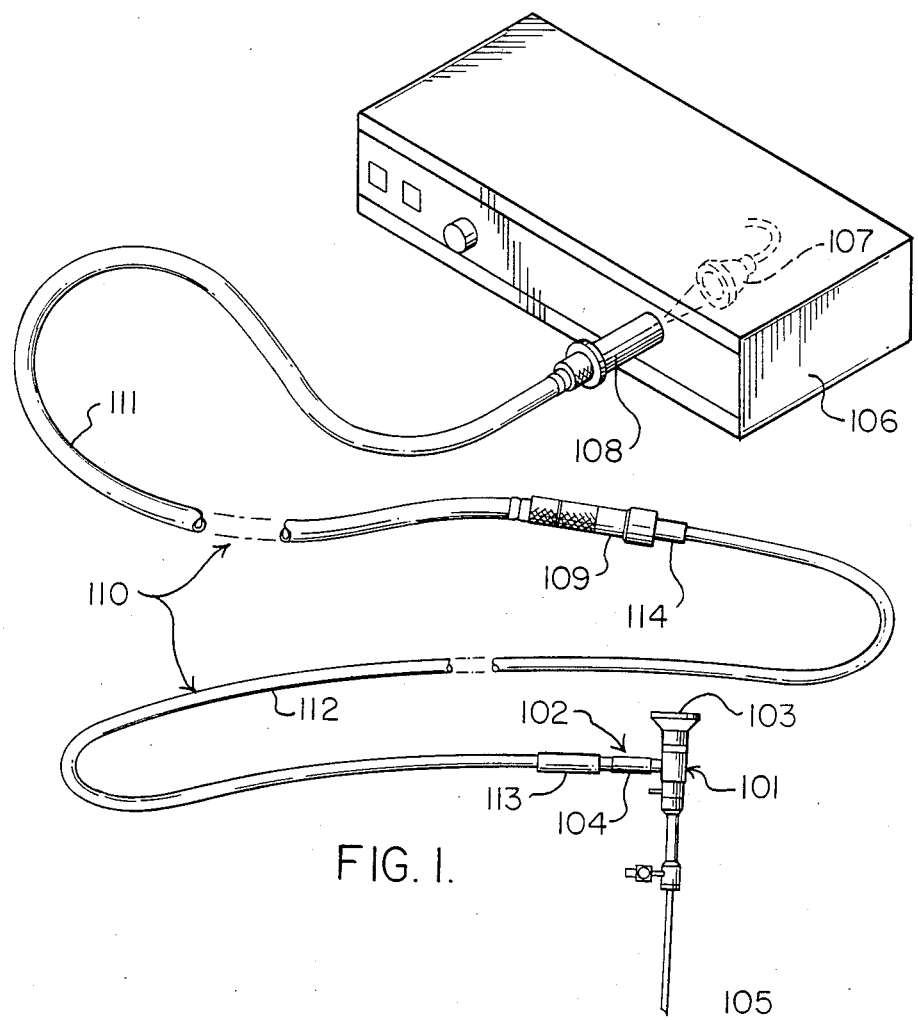
FIG. 1 illustrates the basic architecture of the improved fiber optic light transmission apparatus.

FIG. 1 illustrates the overall architecture of the preferred embodiment of the invention in schematic form. The present invention is demonstrated in the form of a light transmission system that is used for arthroscopic surgical applications. In this environment, the surgeon inserts the probe end 105 of an arthroscope 101 into an incision in the knee joint of the patient in order to ascertain what damage has taken place in this joint. Arthroscopes are well known in the industry and arthroscope 101 can be for example the Zimmer ® Sportscope manufactured by Aspen Labs. Arthroscope 101 provides an optical path from viewing port 103 to probe end 105 via a rod lens or self-focusing fiber optics. Arthroscope 101 may include a camera (not shown) which provides an electronic signal indicative of what the surgeon would see looking through the viewing port 103 of arthroscope 101. The camera transmits its electronic images via a cable to a video display monitor (not shown) in the NTSC Standard 525 lines 30 frames per second format. The video camera is a commercially available apparatus such as the Zimmer ® RGB camera manufactured by Aspen Labs.

In order to provide the light necessary to illuminate the inside of the patient's knee joint, arthroscope 101 is equipped with a light input port 102. This light input port 102 consists of an optically conductive media that is terminated in a connector 104. This enables the surgeon to attach a light source to arthroscope 101 to thereby illuminate the knee joint. The typical commercially available light source consists of a light generator system 106 which contains a high intensity light source 107 and various control circuitry (not shown) that regulates the operation of light source 107 and provide various integrity test functions as are well known in this technology. Light generator apparatus 106 can be the commercially available ZVP ™ Automatic Light Source produced by Aspen Labs. A typical light generator apparatus 106 uses a Gemini 300 Mercury Halide Arc lamp or an Osram HTI Metal Halide Arc lamp that operates at a color temperature of approximately 6000 degrees Kelvin to produce a light output that contains little infrared radiation and approximates sunlight for superior color rendition of the knee joint. This lamp consumes approximately 300 watts of power and operates at a temperature of 1400° Centigrade. The mercury halide arc lamp fires at 20–40,000 volts and its light output and heat output cannot be regulated since it operates in a binary fashion—on or off.

Included in the light transmission system of FIG. 1 is a light guide 110 that serves to optically interconnect light generation apparatus 106 with arthroscope 101. In prior art systems, light guide apparatus 110 is typically constructed from a large diameter optical grade glass optical fiber cable that is constructed from a large number of small diameter individual glass optical fibers. This bundle of fibers is enclosed in a thick chemically resistant medical grade jacket. Both ends of the light guide are terminated in connectors (108, 113) that serve to optically and mechanically interconnect the light guide 110 with the light generation apparatus 106 and the arthroscope 101 respectively. The connectors used on either end of the light guide are generally made from stainless steel due to the fact that they, along with the jacket, must withstand both the corrosive effects of the chemicals used to sterilize the light guide as well as the high temperatures produced by the light source 107. In fact the connector 108 can reach temperatures sufficiently high to ignite flammable materials if placed in proximity thereto or to cause serious burns if improperly handled by operating room personnel.

Light Source

In operation, the light source 107 in light generation apparatus 106 produces a focused, extremely high intensity light beam that is transmitted into the input end of the light guide 110 via the connector 108 interconnection arrangement described above. The light guide 110 is heat resistant and can withstand the extremely high temperatures generated by the light source 107. A typical light source 107 would be a mercury halide arc lamp such as the model 300 produced by Gemini. The operating temperature of such a light source 107 is in the vicinity of four hundred degrees Centigrade. The light generation apparatus 106 is typically equipped with cooling fans to dissipate as much of the heat generated by the light source 107 as possible. Even with sophisticated cooling techniques, the temperature in the vicinity of the end of the light guide 110 will be on the order of four hundred degrees Centigrade. The light source end of the light guide 110 must be in fairly close proximate relationship to the light source 107 in order to maximize the light transmission from the light source 107 to the end of the light guide 110. The light guide 110 itself attenuates light transported therethrough and must be kept to a predetermined length in order to provide a sufficient light output at the arthroscope 101 to illuminate the knee joint at a level that is sufficient to operate the camera. In this application, it is difficult to generate sufficient light and transport this light with minimal loss in an economical fashion to provide the intensity required at the arthroscope 101 or end instrument. Therefore there must be close physical and optical coupling between the end of the light guide 110 and the light source 107.

Improved Fiber Optic Light Transmission Apparatus

In this architecture, the use of plastic optical fibers exclusively to implement the light guide 110 is impractical since the elevated temperatures at the light source 107 would instantly destroy the plastic optical fibers. A typical plastic optical fiber can withstand temperatures on the order of seventy degrees Centigrade. The physical separation required between the light source 107 and the end of the light guide 110 if the light guide 110 were manufactured exclusively from plastic optical fibers would be of such great distance that the optical loss between these two elements would render this configuration impractical. This is due to the fact that the light source produces a focused high intensity beam of light and physical separation, with air as the intervening media, would quickly disperse the light beam to the point where insufficient light would be produced at the end instrument, arthroscope 101.

In order to overcome these problems, the apparatus of the present invention interposes a heat resistant yet optically conductive coupling apparatus 111 between the light source 107 and the end of the plastic optical fiber light guide 112. This coupling apparatus 111 provides high optical transmissivity and maintains the focus of the generated light beam to reduce optical loss between the light source 107 and the end of the plastic optical fiber light guide 112. This coupling apparatus 111 can also withstand the high thermal output of the light source 107 at one end and not couple this heat to the other end where it interconnects with the plastic optical fiber light guide 112. Thus, the coupling apparatus 111 provides heat attenuation to cool the light.

In the preferred embodiment illustrated in FIG. 1, this coupling apparatus 111 is implemented using a glass optical fiber light guide. The glass optical fiber light guide 111, as can be seen from its use as described above, is heat resistant and yet optically highly conductive. This glass optical fiber light guide 111 also is not highly thermally conductive so it does not transmit the heat produced by the light source 107 for any great distance along its length. Thus, the glass optical fiber light guide 111 satisfies the requirements postulated above for the media necessary to interconnect the plastic optical fiber light guide 112 with the light source 107.

The glass optical fiber light guide 111 is connected to the light generation apparatus 106 via the connector 108 located at one end of the glass optical fiber light guide 111. The other end of this standard commercially available glass optical fiber light guide 111 is terminated in a connector 109 that typically is used to connect to arthroscope 101. In the apparatus of FIG. 1, plastic optical fiber light guide 112 is interposed between arthroscope 101 and connector 109 at the end of the glass optical fiber light guide 111. The plastic optical light guide 112 itself is equipped with a connector at either end. Connector 113 is provided on one end of plastic optical light guide 112 to interconnect with connector 109 of the glass optical fiber light guide 111. Connector 114 has a configuration that is similar to connector 104 that terminates the light input port 102 of arthroscope 101. Thus, connector 114 of plastic optical light guide 112 provides a mechanical and optical coupling with connector 109 of glass optical fiber light guide 111. At the other end of plastic optical light guide 112 is a connector 113 that serves to interface with connector 104 of the light input port 102 of arthroscope 101. The light generation apparatus 106 is connected to the coupling apparatus which consists of glass optical fiber light guide 111 which itself is connected to the plastic optical fiber light guide 112 to carry the light from the light source 107 to arthroscope 101.

Light Guide Implementation Details

FIG. 2 illustrates in cross sectional view a typical plastic optical fiber light guide. This light guide 112 is implemented by the use of a plurality of plastic optical fibers 201 which are bundled together inside of jacket 202 made of for example polyethylene, which serves to physically contain the plurality of optical fibers 201, protect the optical fibers 201 from physical damage and provide a covering over the plurality of plastic optical fibers 201. Light guide 112 can for example be a bundle of twenty-one individual plastic optical fibers. A bundle of diameter 4 mm can be constructed of 30 mil diameter individual fibers. These individual fibers are typically manufactured in a concentric double structure comprising a core of transparent polymethyl methacrylate (PMMA) of a high refractive index covered with a thin layer of transparent cladding material of a low refractive index. The light that enters one end of the fiber is reflected off the interface between the core and cladding then discharged at the other end of the fiber. Such a plastic optical fiber is manufactured by Mitsubishi Rayon Co. under the trade name ESKA ™. This plastic optical fiber can withstand a maximum service temperature of 80° Centigrade.

The plastic optical fiber light guide 112 is terminated at one end by a connector 113 manufactured from Delran, for example, which provides a means to mechanically interconnect one end of the plastic optical fiber light guide 112 with the connector 104 attached to the light input port 102 of arthroscope 101. Delran is a thermally resistant material that is approved for medical use although other materials can also be used to implement connector 113, 104. In the embodiment illustrated in FIG. 2, connector 113 is a simple slip on friction fit coupling that interconnects with connector 104. The typical arthroscope connector 104 is a stainless steel bayonet connection that contains a rod lens to optically provide a path for the light provided by light guide 110. Since the plastic optical fiber light guide 112 is inexpensive to manufacture compared to the glass optical fiber light guide 111, the plastic optical fiber light guide 112 can be a disposable item. Therefore, connector 113 can be manufactured from a plastic material since it does not have to be sterilized after each use. The simple slip on arrangement illustrated in FIG. 2 is adequate in terms of precision of mechanical interconnection and durability for its intended use. Similarly, connector 114 serves to mechanically interconnect the other end of the plastic optical fiber light guide 112 with connector 109 attached to one end of the glass optical fiber light guide 111.

Light Guide Interconnection

FIG. 3 illustrates in further detail the interconnection of the glass optical fiber light guide 111 and the plastic optical fiber light guide 112. This illustration provides a cross sectional view of the various details of the connectors 114, 109 and the associated optical fibers. On the righthand side of FIG. 3 is the plastic optical fiber light guide 112 which contains a plurality of plastic optical fibers 201. The plurality of plastic optical fibers 201 is covered by a jacket 202 to protect the plastic optical fibers 201 from damage as described above. Connector 114 is the connector illustrated in FIG. 2. The interconnection of connector 114 and the plurality of plastic optical fibers 201 is accomplished by the use of a metal (medical grade stainless steel) sleeve 301 which mechanically secures the plurality of plastic optical fibers 201 and provides rigid mechanical support for the end of the plurality of plastic optical fibers 201. Sleeve 301 is affixed to the end of the plurality of plastic optical fibers 201 and a potting compound is applied thereto to fill the spaces between the plurality of plastic optical fibers 201 and to provide a mechanically rigid termination for the plurality of plastic optical fibers 201. The potted, bundle of plastic optical fibers is polished to provide the proper optical surface for efficient light transmission. Sleeve 301 is covered with a plastic covering 308 that enables connector 114 to be mechanically force fit onto the sleeve 301. In place of the plastic covering 308 an adhesive can be used to provide a secure connection between connector 114 and sleeve 301. Connector 114 is equipped with a notch 309 to interconnect with a spring 307 that is part of connector 109 as is described below.

Connector 109 serves to mechanically terminate the glass optical fiber light guide 111. The glass optical fiber light guide 111 consists of a large diameter glass optical fiber 302 which is implemented by a large number of individually cladded, very small diameter glass optical fibers. For example, a 4 millimeters cross section glass optical fiber is typically constructed from 5482 individual 40u glass optical fibers. The glass optical fibers are bonded together by for example epoxy potting at each end of the cable using a sleeve to mechanically secure the fibers and provide mechanical support. The length of glass optical fiber cable is then covered by a thick heat resistant and chemically resistant jacket 303. Connector 109 consists of two parts, a connector body 310 and a connector shell 306. Connector body 310 serves to mechanically interconnect connector 109 with the glass optical fiber light guide 111 while the shell 306 provides the mechanical coupling with the connector 104 on the light input port 102 of arthroscope 101 or, in this case, the plastic optical fiber light guide 112. The connector body 310 includes a crimp fitting 304 that mechanically provides a tight fit of connector body 310 to the jacket 303 of the glass optical fiber light guide 111. The glass optical fiber 302 itself extends through the body of connector 310. The connector shell 306 is attached to connector body 310 by a set of mating screw threads 305. The connector shell 306 includes a spring 307 that serves to provide a mechanically secure connection to the connector 104 of the light input port 102 of arthroscope 101. This is a snap fit type of interconnection. Thus, the connector shell 306 provides a snap fit connection to connector 114 of the plastic optical fiber light guide 112 while screw thread 305 enables the user to bring the end of the plastic optical fibers 201 in mechanical juxtaposition with the end of the glass optical fiber 302.

Optical Cross Section

Figure 4:
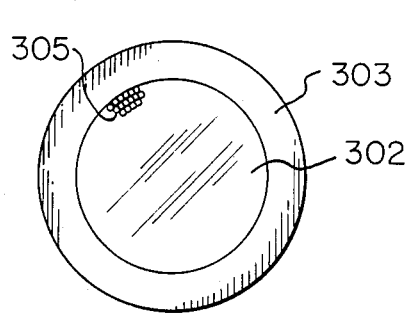
FIGS. 4 and 5 illustrate typical cross sectional views of the heat resistant light conductor and the heat sensitive light conductor respectively.
Figure 5:
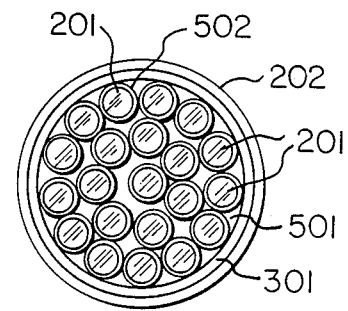

FIGS. 4 and 5 illustrate the Optical cross section of both the glass optical fiber light guide 111 and the plastic optical fiber light guide 112, respectively. FIG. 4 illustrates the end view of the glass optical fiber light guide 111 which shows a circular cross section glass optical fiber 302 covered by its medical grade jacket 303. The glass optical fiber 302 itself contains many individually cladded glass optical fibers 305. Adjacent to FIG. 4 is FIG. 5 which illustrates the optical cross section view of the plastic optical fiber light guide 112. This light guide includes a plurality of plastic optical fibers 201 arranged in a circular cross section which is covered by sleeve 301 and jacket 202. Each individual plastic optical fiber 201 is coated with a cladding 502 (thickness exaggerated). The area between the plurality of plastic optical fibers 201 is filled with a potting compound 501 to provide a mechanically rigid structure.

FIG. 6 illustrates in additional detail the cross section view of the mating arrangement of the glass optical fiber light guide 111 and the plastic optical fiber light guide 112. As can be seen from FIG. 6, the optical cross section diameter of the cylindrical glass optical fiber 302 (x) is less than the optical cross diameter section (y) of the cylindrically arranged plurality of plastic optical fibers 201. Thus, in an optical transmissivity sense, the plastic optical fiber cable 201 can transmit more light than the glass optical fiber cable 302 since it has a greater optical cross section. This is a significant consideration in the configuration illustrated in FIG. 1, since the light supplied by light source 107 is of such great intensity, that it must be transmitted uninterrupted to arthroscope 101. Any obstruction in this light path causes the generation of intense heat since the light generated by light source 107 is of such intensity that any obstruction in the confines of the small optical cross section of light guide 110 would cause the obstruction to absorb a tremendous amount of light energy and generate a resulting large amount of heat. Thus, the optical cross section of the heat sensitive light transmission apparatus, plastic optical fiber light guide 112, must be equal to or greater than the optical cross section of the heat resistant light transmission apparatus, glass optical fiber light guide 111.

It is also important that the mechanical interconnection of the glass optical fiber light guide 111 and the plastic optical fiber light guide 112 provide fairly accurate optical alignment of the two light transmission systems to again prevent the light generating by light source 107 from encountering an obstruction before it reaches arthroscope 101. Thus, as a practical matter it is advantageous to make the optical cross section of the plastic optical light guide 112 greater than the optical cross section of the glass optical fiber light guide 111 to thereby automatically compensate for any optical misalignment due to the mechanical coupling of these two light transmission apparatus. The preferred embodiment of the invention illustrates the use of a circular cross section glass optical fiber light guide 111 although other cross sectional configurations are possible. Also, the plastic optical fiber light guide 112 is illustrated as comprising a plurality of small diameter plastic optical fibers 201. In the illustration, twenty-one small diameter plastic optical fibers 201 are shown although it is obvious that various other diameters and numbers of plastic optical fibers can be used to implement plastic optical fiber light guide 112 as long as the above noted constraints are satisfied. The use of this particular orientation and number of plastic optical fibers 201 is clearly for illustrative purposes and in no way should be construed as a limitation in the implementation of plastic optical fiber light guide 112.

It is evident that the geometry of the glass optical fiber light guide 111 and the plastic optical fiber light guide 112 need not be identical. If the geometry of the two light transmission apparatus do not match, the optical cross section of the heat sensitive light guide should encompass all of the optical cross section of the heat resistant light guide. Thus, the glass optical fiber light guide 111 can be a circular cross section while the cross section of the plastic optical fiber light guide 112 could be rectangular or square in shape as long as the constraint of the optical cross section of the plastic optical fiber light guide 112 is equal to or greater than the optical cross section of the glass optical fiber light guide 111.

Dual Output Ports

Figure 8:
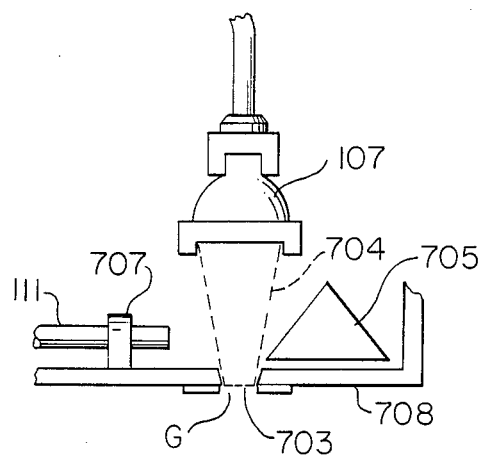
FIGS. 7-9 illustrate the dual light output port configuration of the improved fiber optic light transmission apparatus.
Figure 9:
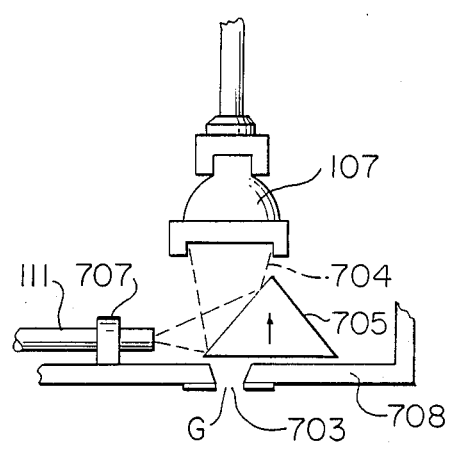
Figure 7:
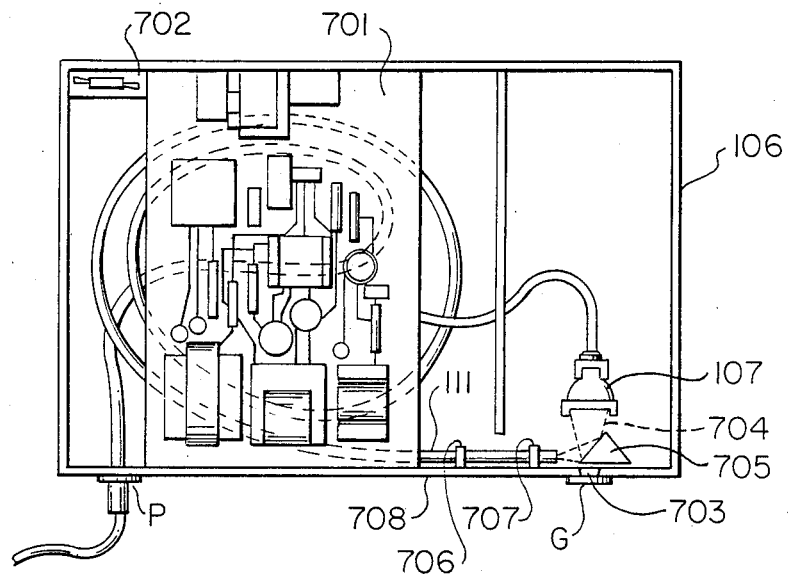

The improved fiber optic light transmission system illustrated in FIG. 1 makes use of a coupling apparatus 111 that is externally connected to light generation apparatus 106. FIGS. 7–9 illustrate an alternative arrangement wherein coupling apparatus 111 is incorporated within light generation apparatus 106. In this configuration, light generation apparatus 106 is equipped with two light output ports, one (G) directly coupled to light source 107 and one (P) coupled to the output of coupling apparatus 111.

FIG. 7 illustrates a top view of light generation apparatus 106 with the cover removed therefrom. Light source 107 is electrically connected to a printed circuit board 701 that contains the control circuitry that regulates the operation of light source 107. A fan 702 is included to provide an air flow over printed circuit board 701 and light source 107 to cool this apparatus. In this configuration, the glass optical fiber light guide used to implement coupling apparatus 111 is placed in light generation apparatus 106 and connector 113 is terminated on the front panel 708 of light generation apparatus 106. The glass optical fiber light guide 111 can be placed under printed circuit board 701 such that the source end 711 of the glass optical fiber light guide 111 is located in front of light source 107 and 90° to one side thereof. Brackets 706, 707 secure the source end 711 in position to receive light beam 704. Thus, the front panel 708 of light generation apparatus 106 includes two light output ports: one (G) aperture 703 located directly in front of light source 107 and a second (P) at connector 113 located at one end of the glass optical fiber light guide 710.

In order to control the activation of these two light output ports (G, P), a switching mechanism is included in light generation apparatus 106. This switching mechanism includes a reflective surface, such as a heat resistant front surface mirror (or a prism) 705 that serves to switch light beam 704 from aperture 703 to glass optical fiber light guide 111. FIG. 8 illustrates front surface mirror 705 in position to enable light beam 704 to illuminate the first port (G) at aperture 703. Light source 107 is a reflector lamp such as the Osram HTI 400 W/24.

This lamp includes a computer-calculated cold-light mirror similar in shape to an ellipse. The mirror not only bundles the light from the discharge arc of the lamp electrodes but also reaches, through mixing, a very even illumination of an aperture. The size of the aperture is approximately 7 mm. The light beam 704 produced by light source 107 is projected into aperture 703 in the front panel 708 of light generator apparatus 106. The glass optical fiber 302 contained within coupling apparatus 111 is terminated by connector 108 such that the polished end of glass optical fiber 302 is located at the focal point of the light beam 704. This configuration is the typical light generation apparatus 106 architecture.

The switching mechanism includes a locking slide arrangement (not shown) that, when operated, precisely locates front surface mirror 705 in the path of light beam 704 as illustrated in FIG. 9. In this position, front surface mirror 705 deflects light beam 704 through a 90° change of direction such that the focal point of light beam 704 now is located at one end of the glass optical fiber light guide 111. This positioning of front surface mirror 705 now causes the port (P) terminated in connector 113 to be illuminated by light beam 704.

This switchable light beam configuration provides additional flexibility to the user of light generation apparatus 106. A plastic optical fiber light guide 112 can be directly connected to port P, a glass optical fiber light guide 111 can be directly connected to port G, or a plastic optical fiber light guide 112 can be connected to port G via a glass optical fiber light guide 111 as illustrated in FIG. 1.

While a specific embodiment of this invention has been disclosed, it is expected that those skilled in the art can and will design alternate embodiments of this invention that fall within the scope of the appended claims.

I claim:

1. In a light transmission system having a high thermal output light source, an improved light transmission apparatus comprising:
   heat sensitive light conductor means having an input with a first optical cross-section and an output for transmitting light applied to said input to said output; and
   means for optically coupling and thermally decoupling said input of said heat sensitive light conductor means to the high thermal output light source, said coupling means having a second optical cross-section no greater than said first optical cross-section coupled to said input of said heat sensitive light conductor means.

2. The apparatus of claim 1 wherein said coupling means includes;
   glass optical fiber light guide means interposed between said high thermal output light source and said input of said heat sensitive light conductor means.

3. The apparatus of claim 2 wherein said glass optical fiber light guide means includes:
   one or more glass optical fibers, having an input for receiving light and an output for outputting said light received at said input;
   first connector means connected to and optically coupling said input of said glass optical fiber light guide means to said high thermal output light source; and
   second connector means connected to an optically coupling said output of said glass optical fiber light guide means and said heat sensitive light conductor means.

4. The apparatus of claim 3 wherein said first optical cross-section has an area x and said second optical cross-section has an area no greater than x.

5. The apparatus of claim 4 wherein the geometry of said first optical cross-section is selected to completely encompass said second optical cross-section.

6. The apparatus of claim 1 wherein said heat sensitive light conductor means includes one or more plastic optical fibers, said coupling means includes:
glass optical fiber light guide means interposed between said high thermal output light source and said input of said heat sensitive light conductor means.

7. The apparatus of claim 6 wherein said first optical cross-section has an area x and said second optical cross-section has an area no greater than x.

8. The apparatus of claim 7 wherein the geometry of said first optical cross-section is selected to completely encompass said second optical cross-section.

9. The apparatus of claim 6, wherein said heat sensitive light conductor means further includes:
sleeve means located at at least one end of said heat sensitive light conductor means for mechanically securing said one or more plastic optical fibers in a bundle; and
potting means surrounding said one or more plastic optical fibers and located substantially within said sleeve means for adhesively bonding said one or more plastic optical fibers together.

10. The apparatus of claim 6 wherein said heat sensitive light conductor means further includes:
jacket means surrounding said one or more plastic optical fibers for mechanically bundling said one or more plastic optical fibers into a cable form.

11. In a light transmission system having a high thermal output light source, an improved light transmission apparatus comprising
heat sensitive light conductor means having an input and an output for transmitting light applied to said input to said output;
means for optically coupling and thermally decoupling said input of said heat sensitive light conductor means to said high thermal output light source;
light port means for mechanically and optically coupling said high thermal output light source to a heat resistant light conductor; and
means for selectively switching the light output of said high thermal output light source to either said light port means or said coupling means.

12. The apparatus of claim 11 wherein said switching means includes:
means, interposable between said high thermal output light source and said light port means, for redirecting said light output from said high thermal output light source to said coupling means.

13. A light transmission apparatus for use in surgery to transmit light from a high thermal output light source comprising
heat sensitive light conductor means including a plurality of heat sensitive optical fibers having an input and an output for transmitting light received at said input to said output; and
heat resistant light conductor means including a plurality of heat resistant optical fibers having an input optically coupled to the high thermal output light source and an output optically coupled to said heat sensitive light conductor means input for thermally decoupling said heat sensitive light conductor means and the high thermal output light source.

14. The apparatus of claim 13 wherein said heat resistant optical fibers include a plurality of glass optical fibers and said heat sensitive optical fibers include a plurality of plastic optical fibers.

15. The apparatus of claim 14 wherein said heat resistant light conductor means further includes
first connector means connected to and optically coupling said input of said glass optical fibers to the high thermal output light source; and
second connector means separate from said first connector means connected to and optically coupling said output of said glass optical fibers to and said plastic optical fibers.

16. The apparatus of claim 15 wherein said heat sensitive light conductor means further includes
sleeve means located at at lest one end of said heat sensitive light conductor means for mechanically securing said plurality of plastic optical fibers in a bundle; and
potting means surrounding said plurality of plastic optical fibers and located substantially within said sleeve means for adhesively bonding said plurality of plastic optical fibers together.

17. The apparatus of claim 15 wherein said heat sensitive light conductor means further includes
jacket means surrounding said plurality of plastic optical fibers for mechanically bundling said plurality of plastic optical fibers into a cable form.

18. In a light transmission apparatus that includes a high thermal output light source that produces a beam of light, apparatus for optically interconnecting a plastic optical fiber cable having one or more light conductors and an optical crosssection of x to said light source comprising:
heat resistant light conductor means having an input and an output and an optical cross-section less than x, said input optically coupled to said light source for transmitting said beam of light to said output; and
means for optically interconnecting said output of said hat resistant light conductor means with one end of said plastic optical fiber cable for transmitting said beam of light from said output of said heat resistant light conductor means to said one end of said plastic fiber optic cable.

19. The apparatus of claim 18 wherein said heat resistant light conductor means includes:
one or more glass optical fibers having an input for receiving said beam of light and an output for outputting said beam of light received at said input.

20. The apparatus of claim 19 wherein said heat resistant light conductor means further includes
first connector means connected to and optically coupling said input of said one or more glass optical fibers to said light source for transmitting said beam of light from said light source to said input of said one or more glass optical fibers; and
second connector means connected to and optically coupling said output of said one or more glass optical fibers and said plastic optical fiber cable for transmitting said beam of light from said output of said one or more glass optical fibers to said plastic optical fiber cable.

21. The apparatus of claim 18 further including:

connector means for optically coupling a glass optical fiber light conductor to said beam of light; and means for selectively switching said beam of light to either said connector means or said input of said heat resistant light conductor means.

22. The apparatus of claim 21 wherein said switching means includes:

means for redirecting said beam of light from said connector means to said input of said heat resistant light conductor means.

23. In a light transmission system having a high temperature mercury vapor discharge lamp that produces a beam of light, apparatus for interconnecting said beam of light to a plastic optical fiber cable, having one or more light conductors and an optical crosssection of x, comprising:

high temperature light conductor means including one or more glass optical fiber light conductors of optical cross-section no greater than x, and having an input and an output for conducting light applied to said input to said output;

means for optically coupling said input of said high temperature light conductor means to said beam of light; and connector means for optically coupling said output of said high temperature light conductor means and one end of said plastic optical fiber cable for transmitting said beam of light from said output of said high temperature light conductor means to said one end of said plastic optical fiber cable.

24. The apparatus of claim 23 wherein said high temperature light conductor means has an optical cross-section area of x, said plastic optical fiber cable includes:

one or more plastic optical fibers of optical cross-section area at least x.

25. The apparatus of claim 24 wherein the geometry of said optical cross-sect of said high temperature light conductor means is selected to be completely encompassed by the optical cross-section of said one or more glass optical fibers.

26. An arthroscopic apparatus for producing illumination at a probe tip of an arthroscope comprising:

light generation apparatus including a high thermal output light source for producing a high intensity light beam;

glass fiber optic light guide means having first and second ends for transmitting light therebetween;

first connector means connected to said first end of said glass fiber optic light guide means for optically interconnecting said first end with said light generation apparatus to apply said high intensity light beam to said first end of said glass fiber optic light guide means;

plastic fiber optic light guide means having first and second ends for transmitting light therebetween;

means for mechanically and optically interconnecting said second end of said glass fiber optic light guide means and said first end of said plastic fiber optic light guide means to transmit said high intensity light beam from said second end of said glass fiber optic light guide means to said first end of said plastic fiber optic light guide means; and second connector means connected to said second end of said plastic fiber optic light guide means for mechanically and optically interconnecting said second end of said plastic fiber optic light guide means and said arthroscope to transmit said high intensity light beam from said second end of said plastic fiber optic light guide means to said arthroscope.

27. The apparatus of claim 26 wherein the geometry of said optical cross-section of said plastic fiber light guide means is selected to completely encompass the optical cross-section of said glass fiber optic light guide means.

28. The apparatus of claim 26, wherein said plastic fiber optic light guide means further includes:

a plurality of plastic optical fibers;

sleeve means located at at least one end of said plastic fiber optic light guide means for mechanically securing said plurality of plastic optical fibers in a bundle; and potting means surrounding said plurality of plastic optical fibers and located substantially within said sleeve means for adhesively bonding said plurality of plastic optical fibers together.

29. The apparatus of claim 28 wherein said plastic fiber optic light guide means further includes:

jacket means surrounding said plurality of plastic optical fibers for mechanically bundling said plurality of plastic optical fibers into a cable form.

30. The apparatus of claim 26 further including:

third connector means for optically interconnecting a second glass fiber optic light guide to said high intensity light beam; and means for selectively switching said high intensity light beam to either said third connector means or said first connector means.

31. The apparatus of claim 30 wherein said switching means includes:

front surface mirror means for redirecting said high intensity light beam from said third connector means to said first connector means.

* * * * *